(12) United States Patent
Yokoyama et al.

(10) Patent No.: US 8,012,430 B2
(45) Date of Patent: Sep. 6, 2011

(54) METHODS FOR PRODUCING MICROCHANNEL CHIPS, MICROCHANNEL CHIPS, METHODS FOR SEPARATING BIOMOLECULES USING THE MICROCHANNEL CHIPS, AND ELECTROPHORETIC APPARATUS HAVING THE MICROCHANNEL CHIPS

(75) Inventors: Kenji Yokoyama, Ibaraki (JP); Satoshi Koide, Ibaraki (JP); Koji Sakairi, Tokyo (JP); Kazuyoshi Yano, Tokyo (JP); Isao Karube, Kanagawa (JP)

(73) Assignees: National Institute of Advanced Industrial Science and Technology, Tokyo (JP); Katayanagi Institute, Tokyo (JP); Toppan Printing Co., Ltd., Tokyo (JP)

( * ) Notice: Subject to any disclaimer, the term of this patent is extended or adjusted under 35 U.S.C. 154(b) by 984 days.

(21) Appl. No.: 10/591,335

(22) PCT Filed: Mar. 3, 2005

(86) PCT No.: PCT/JP2005/003604
§ 371 (c)(1),
(2), (4) Date: Oct. 26, 2007

(87) PCT Pub. No.: WO2005/084794
PCT Pub. Date: Sep. 15, 2005

(65) Prior Publication Data
US 2010/0101953 A1    Apr. 29, 2010

(30) Foreign Application Priority Data
Mar. 4, 2004    (JP) .................................. 2004-060215

(51) Int. Cl.
*B01L 3/00* (2006.01)
*G01N 27/453* (2006.01)
(52) U.S. Cl. ........................................ 422/503; 204/601
(58) Field of Classification Search .......... 204/600–605, 204/450–455; 422/502–508
See application file for complete search history.

(56) References Cited

U.S. PATENT DOCUMENTS

| 5,989,402 | A * | 11/1999 | Chow et al. ................... 204/601 |
| 6,499,499 | B2 * | 12/2002 | Dantsker et al. ................... 137/1 |
| 6,841,193 | B1 * | 1/2005 | Yang et al. ..................... 427/230 |
| 7,010,964 | B2 * | 3/2006 | Karp et al. ..................... 73/61.52 |
| 7,220,345 | B2 * | 5/2007 | Bohn et al. ..................... 204/600 |
| 2003/0116437 | A1 * | 6/2003 | Burns et al. .................... 204/453 |

FOREIGN PATENT DOCUMENTS
JP    5-503989    6/1993
(Continued)

OTHER PUBLICATIONS

Mikkers et al., "High-Performance Zone Electrophoresis," J. Chromatogr. 169:11-20 (1979).

(Continued)

*Primary Examiner* — Alex Noguerola
(74) *Attorney, Agent, or Firm* — Nixon Peabody LLP (57) ABSTRACT

The methods for producing microchannel chips of the present invention comprise the steps of shielding substrate surfaces on which groove-like channels have been formed, using a mask that exposes the channels, and then forming polymer membranes on the exposed surfaces of the substrates; and the step of laminating cover materials onto the side of the substrate surfaces on which the channels have been formed.

16 Claims, 4 Drawing Sheets

Formed membrane

FOREIGN PATENT DOCUMENTS

| | | |
|---|---|---|
| JP | 7-506432 | 7/1995 |
| JP | 9-504375 | 4/1997 |
| JP | 2000046797 A | 2/2000 |
| JP | 2001-252896 | 9/2001 |
| JP | 2002148236 A | 5/2002 |
| JP | 2003107080 A | 4/2003 |
| JP | 2003121453 A | 4/2003 |
| JP | 2003220330 A | 8/2003 |
| JP | 2004028959 A | 1/2004 |
| JP | 2004061319 A | 2/2004 |
| WO | 91/06851 A1 | 5/1991 |
| WO | 93/22665 A1 | 11/1993 |
| WO | 95/16911 A1 | 6/1995 |
| WO | WO 01/26812 A1 * | 4/2001 |
| WO | 2004008132 A1 | 1/2004 |

OTHER PUBLICATIONS

Tsai et al., "Application of Plasma-Polymerized Films for Isoelectric Focusing of Proteins in a Capillary Electrophoresis Chip," Analyst 128(3):237-244 (2003).

* cited by examiner

FIG. 1

Formed membrane

METHODS FOR PRODUCING MICROCHANNEL CHIPS, MICROCHANNEL CHIPS, METHODS FOR SEPARATING BIOMOLECULES USING THE MICROCHANNEL CHIPS, AND ELECTROPHORETIC APPARATUS HAVING THE MICROCHANNEL CHIPS

This application is a national stage application under 35 U.S.C. §371 from PCT Application No. PCT/JP2005/003604, filed Mar. 3, 2005, which claims the priority benefit of Japanese Application No. JP 2004-060215, filed Mar. 4, 2004, which is hereby incorporated by reference in its entirety.

TECHNICAL FIELD

The present invention relates to methods for producing microchannel chips. The present invention also relates to microchannel chips, and to methods for separating biomolecules and electrophoretic apparatus that use the microchannel chips.

BACKGROUND ART

To date capillary electrophoresis and microchannel chip electrophoresis have been widely researched since they are exceptionally good methods when separating and analyzing trace amounts of a biomolecule, and allow automatization and speed-up of analyses (Non-patent Document 1).

Materials generally used for capillary electrophoresis or microchannel chip electrophoresis include glass, but glass has many problems to be solved when separating proteins.

For example, capillary electrophoresis or microchannel chip electrophoresis apparatus made of glass is influenced by electroosmotic flow.

Thus, for example, to prevent the generation of electroosmotic flow inside capillaries, the inner walls of the capillaries have been coated with polymers (Patent Documents 1, 2, and 3). Coating methods including chemical immobilization of compounds onto surfaces and physical absorption have been attempted.

Coating with silane-coupling agents are known chemical coating methods when using glass capillaries or microchannel chips. These methods can very strongly coat the inside of microchannels since the silane-coupling agents bind covalently. However, homogenous coating is difficult, and capillaries or microchannel chips with high reproducibility cannot be produced. Further, the coating method uses chemical reactions and is thus difficult, making manufacturing processes ineffective.

Another known coating method is a physical coating method where the coating agent flows through the channels. For example, there are methods in which an electrophoresis buffer mixed with a coating agent flows through to coat the channels. These methods are very convenient, but since adsorption is based on electrostatic or hydrophobic interactions, the absorptive conditions are very weak and coatings can be easily detached, which is problematic. Further, since electrostatic interactions are easily influenced by pH, they have limited application.

Thus, methods for applying homogenous and stable coating on substrate surfaces are required. For example, the entire substrate surface of a chip with microchannels on the surface of a glass substrate has been coated with a plasma-polymerized membrane (Non-patent Document 2).

However, extremely high temperatures (e.g. 500° C. to 600° C.) are required when coating a glass substrate and a cover with a plasma-polymerized membrane, and there are cases where the plasma-polymerized membrane deteriorates upon attempting to laminate the substrate and cover using thermocompression bonding. Methods for using adhesives to bind substrates and cover materials have thus been adopted (Non-patent Document 2); however, use of adhesives can result in extrusion of the adhesive into microchannels, depending on the amount used or the site of application, and thus production processes controlling the amount of adhesive used, the sites of application, and the like can become complicated.

[Non-patent Document 1] Journal of Chromatography (F. E. P. Mikkers, F. M. Everaerts, Th. P. E. M. Veerheggen, J. Chromatogr.). 169, 11, 1979

[Non-patent Document 2] Analyst, 2003, 128, 237-244

[Patent Document 1] Japanese Patent Kohyo Publication No. (JP-A) H/S5-503989

[Patent Document 2] Japanese Patent Kohyo Publication No. (JP-A) H/S 7-506432

[Patent Document 3] Japanese Patent Kohyo Publication No. (JP-A) H/S 9-504375

DISCLOSURE OF THE INVENTION

Microchannel chips are generally obtained by laminating cover materials to substrates with channels on their surface; however, the present inventors discovered that coating the entire substrate surface with a polymer membrane such as a plasma-polymerized membrane, a surface-polymerized membrane, or the like could weaken or reduce the adhesive strength of the lamination, and that the medium flowing in the channels could extrude from the channels into the gaps between the substrate and the cover (not publicly known at the time of filing the present application).

Thus, an objective of the present invention is to provide convenient methods for producing microchannel chips, wherein the methods can improve adhesive strength when laminating substrates and cover materials when the substrate surface is coated with a polymer membrane.

The present inventors conducted dedicated studies to achieve the objective described above, and discovered that the processes described below can improve adhesive strength when laminating cover materials to substrates. The inventors also discovered that convenient methods for producing microchannel chips can be provided, and thus completed the present invention. Specifically, the present invention includes the following:

[1] a method for producing a microchannel chip, comprising the steps of:
  a) shielding a surface of a substrate, on which a groove-like channel has been formed, with a mask that exposes the channel,
  b) forming a polymer membrane on the exposed surface of the substrate; and
  c) laminating a cover material on to the substrate surface on which the channel has been formed;

[2] the method of [1], comprising the step of forming a polymer membrane on the side of the cover material surface that will be laminated to the substrate;

[3] the method for producing the microchannel chip of [2], wherein when a polymer membrane is formed on the side of the cover material surface that will be laminated to the substrate, the polymer membrane is formed on an exposed surface of the cover material by shielding the cover material surface with a mask, the exposed area of which is partially or entirely identical in shape to the mask for the substrate;

[4] the method of any one of [1] to [3], wherein the polymer membrane on the substrate surface is:
   (a) a plasma-polymerized membrane formed by plasma polymerizing a plasma-polymerizable monomer on the substrate surface,
   (b) a surface-polymerized membrane formed by polymerizing a polymerizable monomer on the substrate surface, or
   (c) a polymer-bound membrane formed by binding a polymer compound onto the substrate surface;

[5] the method of any one of [1] to [4], wherein the polymer membrane on the substrate surface is a plasma-polymerized membrane;

[6] the method of any one of [2] to [5], wherein the polymer membrane on the cover material surface is:
   (a) a plasma-polymerized membrane formed by plasma polymerizing a plasma-polymerizable monomer on the cover material surface,
   (b) a surface-polymerized membrane formed by polymerizing a polymerizable monomer on the cover material surface, or
   (c) a polymer-bound membrane formed by binding a polymer compound onto the cover material surface;

[7] the method of any one of [2] to [6], wherein the polymer membrane on the cover material surface is a plasma-polymerized membrane;

[8] the method of any one of [2] to [7], wherein the polymer membrane formed on the substrate surface and the polymer membrane formed on the cover material surface are identical polymer membranes;

[9] the method of any one of [1] to [8], wherein the lamination is performed by pressure bonding or thermocompression bonding;

[10] the method of any one of [1] to [9], wherein at least either one of the substrate or the cover material is a plastic;

[11] the method of any one of [1] to [10], wherein the substrate and the cover material are plastics;

[12] the method of [11], wherein both the substrate and the cover material are a thermoplastic resin, and the laminating process comprises a method in which the substrate and the cover material are attached by thermocompression bonding;

[13] the method of [12], wherein thermocompression bonding is performed at 200° C. or less;

[14] the method of [10], wherein one of the substrate or the cover material is a silicon resin, and the other is a glass or a plastic, and the laminating process comprises a method in which the substrate and the cover material are attached by pressure bonding;

[15] the method of any one of [1] to [14], wherein the mask is either a photoresist-mask or a metal mask;

[16] a microchannel chip made by laminating a cover material to a channel-side surface of a substrate on which a channel has been formed, wherein a part or the entire surface of the channel on the substrate surface is coated with a polymer membrane;

[17] the microchannel chip of [16], wherein the substrate-side surface of the cover material is coated with a polymer membrane;

[18] the microchannel chip of [17], wherein an area on the substrate-side surface of the cover material, which is opposite an area of the substrate on which a polymer membrane is formed, is coated with a polymer membrane partially or entirely identical in shape to that on the part of the substrate on which polymer membrane is formed;

[19] a method for separating biomolecules, comprising the steps of:
   a) adding a biomolecule to be analyzed to a microchannel chip made by laminating a cover material to a channel-side surface of a substrate on which a channel has been formed, and coating a surface of the channel on the substrate surface with a polymer membrane; and
   b) applying a separation pressure to a separating medium;

[20] the method of [19], wherein the separation pressure is provided by electrophoresis;

[21] the method of [20], wherein the electrophoresis is capillary electrophoresis;

[22] the method of any one of [19] to [21], wherein the biomolecule is a protein; and

[23] an apparatus for electrophoretic analysis comprising the following components:
   a) a microchannel chip made by laminating a cover material to a channel-side surface of a substrate on which a channel has been formed, and coating a surface of the channel on the substrate surface with a polymer membrane,
   b) a support used to retain the microchannel chip, and
   c) electrodes used to apply a voltage to the microchannel chip retained by the support.

BRIEF DESCRIPTION OF THE DRAWINGS

In FIG. 4, A shows results for chips with plasma-polymerized membranes (HMDS), while B shows results for chips without formed membranes.

BEST MODE FOR CARRYING OUT THE INVENTION

Methods for Producing Microchannel Chips

The methods for producing the microchannel chips of the present invention comprise the steps of: shielding a surface of a substrate, on which groove-like channels have been formed, with a mask that exposes the channels, and forming a polymer membrane on the exposed surface of the substrate; and then laminating a cover material on to the substrate surface on which the channels were formed.

In this case, the masks that expose the channels are preferably masks that expose entire channels or the vicinity of the channels, and the smaller the exposed neighboring area, the more preferable.

The type of mask is not limited; for example, photoresist masks, metal masks and the like may be used.

Microchannel chips thus obtained have outstanding adhesive strength when laminating substrate surfaces with cover materials, because the channels on the substrate surface are coated with polymer membrane, while the remaining area is not.

In such cases, the methods may comprise a step of forming a polymer membrane on the side of a surface of a cover material that will be laminated on to an above substrate. That is, polymer membranes may be formed on the surfaces of both the substrate and the cover material. The ability to resolve samples to be separated using a microchannel chip can be enhanced if a polymer membrane is also formed on a cover material surface.

When forming polymer membranes on cover material surfaces, the polymer membranes are preferably formed on exposed surfaces of the cover materials by shielding the above cover material surfaces with masks, the exposed areas of which are partially or entirely identical in shape to a mask for an above substrate.

In such cases, the smaller the exposed area of cover material, the more preferable; however, it is more preferable that the entire exposed area of an above substrate mask be identical in shape to the exposed area of the cover material.

To improve separability, polymer membranes may be formed in various patterns and gradients in the channels provided on substrate surfaces, or on cover material surfaces. In such cases, for example, the shape of the polymer membranes formed on the side of the cover material may be different from the shape of the substrate masks.

The microchannel chips thus obtained have outstanding adhesive strength when laminating substrates with cover materials since both the substrate and cover material surfaces have some areas that are not coated with polymer membranes.

Substrates are preferably laminated with cover materials such that the polymer membranes coated on to the substrate and cover material surfaces precisely overlap each other.

Preferably, polymer membranes formed on substrate surfaces are any one of
(a) plasma-polymerized membranes formed by plasma polymerizing plasma-polymerizable monomers on substrate surfaces,
(b) surface-polymerized membranes formed by polymerizing polymerizable monomers on substrate surfaces, or
(c) polymer-bound membranes formed by binding polymer compounds onto substrate surfaces. Plasma-polymerized membranes are the most preferable of these. More homogeneous and stable membranes can be formed when using plasma polymerized-membranes.

Preferably, the polymer membranes formed on the above cover material surfaces are any one of:
 (a) plasma-polymerized membranes formed by plasma polymerizing plasma-polymerizable monomers on cover material surfaces,
 (b) surface-polymerized membranes formed by polymerizing polymerizable monomers on cover material surfaces, or
 (c) polymer-bound membranes formed by binding polymer compounds onto cover material surfaces.
Plasma-polymerized membranes are the most preferable of these. More homogeneous and stable membranes can be formed when using plasma polymerized-membranes.
Substrates and Cover Materials When polymer membranes are also formed on cover materials, there is no particular limitation as to the combinations of types of polymer membranes provided on the substrates and cover materials, and either the same or different types of polymer membranes may be used. Preferably, the polymer membrane formed on the above substrate surface and the polymer membrane formed on the above cover material surface are the same type. When the same type of polymer membrane is used, the polymer membranes are preferably plasma-polymerized membranes, and of these, plasma-polymerized membranes made from the same monomer materials are more preferable.

The above substrates may be composed of any material. In the present invention, a surface of the channels formed on a substrate surface has been at least reformed by a plasma-polymerized membrane, a surface polymerized membrane, or a polymer-bound membrane. Thus, the material of the substrates themselves does not directly affect the results of separation by electrophoresis and the like. Therefore, any material fulfilling the following minimum requirements can be selected:
 it resists the heat generated from electrophoresis and the like;
 it has a certain physical strength;
 it is an insulator.

In general, transparent materials are used as substrates. The use of transparent materials allows observation from outside. Specifically, for example, glasses, plastics and the like can be used as the materials.

The plastics include, for example, thermoplastic resins, silicon resins, and the like.

Thermoplastic resins include, for example, poly(meth) acrylate esters such as polymethyl methacrylate (PMMA); polycarbonates (PC); polyethyleneterephthalates (PET); polyvinyl compounds such as polyethylene and polypropylene; polystyrenes and so on.

The heat deformation temperature depends on the types of thermoplastic resin, and is preferably 200° C. or less, more preferably 150° C. or less, and even more preferably 120° C. or less. These temperature ranges can prevent deterioration in the performance of the polymerized membranes.

Silicon resins include silicon rubbers such as polydimethyl siloxane (PDMS). Use of such silicon resins enables the substrate surface or cover material surface to have adhesiveness and to adhere upon pressure bonding.

The substrates are preferably planar basal plates in tabular shapes. The substrates are preferably about 1 mm to 20 mm thick, for example, but are not limited thereto.

Materials with qualities similar to those of the above substrates can be used for the above cover materials. Since cover materials are for covering substrates, a cover material is preferably the same shape and size as a substrate.

The cover materials are preferably about 1 mm to 20 mm thick, for example, but are not limited thereto.

Combinations of substrate and cover material are not specifically limited, and either the same or different materials may be used.

Of these, it is preferable that at least one of the above substrate or the above cover material is plastic.

Further, it is preferable that both the above substrate and cover material are plastics, an in such cases, both are preferably thermoplastic resins.

When either one of the above substrate or cover material is a silicon resin, the other may be a glass or plastic, and is preferably a plastic.

For example, when both the above substrate and cover material are thermoplastic resins, the above lamination method can be a method of thermocompression bonding the substrate and the cover material. The temperature for thermocompression bonding depends on the types of plastics used, and is preferably 200° C. or less, more preferably 150° C. or less, and even more preferably 120° C. or less.

Furthermore, for example, when one of the above substrate or cover material is silicon resin and the other is either plastic or glass, the lamination method can be a method of pressure bonding the substrate and the cover material.

Such preferable combinations of substrates and cover materials (substrate:cover material or cover material:substrate) include the following:

PMMA:PMMA, PDMS:PDMS, PDMS:PMMA, PDMS: glass, PET:PET, PMMA:PET, PDMS:PET, PC:PC, PDMS: PC, PMMA:PC, PS:PS, PDMS:PS, PMMA:PS.

Of these, the combinations of PMMA:PMMA, PDMS: PDMS, PDMS:PMMA, PMMA:PET, PDMS:PET, PDMS: PC, PMMA:PC, PDMS:PS, PMMA:PS and the like can be preferably used.

Of these, combinations of PDMS with other plastics, and PMMA with PMMA are particularly preferable.

The combinations listed above enable adhesion with superior adhesive strength at low temperatures, and even without use of adhesive agents. Specifically, by properly combining such materials, the substrate and cover material can be laminated by pressure bonding or thermocompression bonding as described above.

Furthermore, in the methods for producing microchannel chips of the present invention, these plastics can exert optimal adhesive efficacy since the masks minimize the area on the substrate surface on which the polymer membrane is formed.
Channels The channels are grooves formed on substrate surfaces. For example, the grooves may be as narrow as 1 µm to 100 µm. The cross-sections of the grooves may be polygonal, such as triangular and rectangular, U-shaped or semicircular. Such microstructural grooves can be made on substrates such as glasses and plastics by the following procedures:

wet etching methods of semiconductor processing technologies (methods using hydrofluoric acid)

dry etching methods of semiconductor processing technologies (ion sputtering, reactive-ion etching (ICP etching and others))

laser drilling dicing saw

Microstructures of any shape can be readily produced using the methods of wet etching, dry etching, or laser drilling. For example, technologies used in making grooves with widths and depths of 10 µm to 100 µm on glass surfaces are known.

For example, the present inventors succeeded in producing microchannels using reactive-ion etching. Etching with high selectivity or high etch rates can be achieved by using different types of etching gases, depending on the substrate materials.

The grooves formed on substrate surfaces can be made into a closed system by adding cover materials on it.

Grooves can also be formed on the surfaces of the cover materials. In such cases, the grooves are preferably formed such that they overlap the grooves formed on the substrate.

Furthermore, connection channels for supplying samples and separation media to the grooves can be formed by making holes in the cover materials at positions that overlap the grooves formed on the substrates or cover materials. Alternatively, holes made in the cover materials can be used as reservoirs for holding samples or buffers.
Polymer Membranes The methods for producing the microchannel chips of the present invention comprise the steps of shielding a substrate surface on which groove-like channels have been formed, with a mask that exposes the entirety of the channels, and then forming a polymer membrane on the exposed surface of the substrate. The methods may also comprise the step of forming a polymer membrane on a cover material surface, on the side to be laminated to the substrate. As previously described, the polymer membranes include plasma-polymerized membranes, surface-polymerized membranes or polymer-bound membranes.

Plasma polymerization enables the formation of plasma-polymerized membranes on micro-grooved surfaces. In addition, plasma polymerization produces highly homogeneous membranes. Thus, it can prevent the generation of pinholes on substrate surfaces, and enables the production of highly reliable substrates for separation analyses.

Surface polymerization enables the formation of desired polymerized membranes on desired substrate surface areas, with reduced membrane peeling.

Furthermore, polymer-bound membranes in which polymer compounds are bound to substrate surfaces enable the formation of desired polymer membranes on desired substrate surface areas while controlling membrane thickness.

Substrates or cover materials that have been coated with these plasma-polymerized membranes, surface-polymerized membranes, or polymer-bound membranes can be prepared by conventional methods. Each of the membranes are explained below.
Plasma-Polymerized Membranes Specifically, plasma polymerization is a method for forming membranes directly on to the surfaces of supports by polymerizing monomeric compounds using plasma excitation in a vacuum. Plasma-polymerized membranes with various properties can be produced by changing the constituent monomeric compounds. In principle, any type of monomer can be used for polymerization. Generally, formation of polymers requires cleavage of double bonds; however, polymerization reactions take place via many active species as the monomeric substances become fragmented in the plasma.

Any types of monomers may be used to form the plasma-polymerized membranes of the present invention, as long as they can form polymer membranes that confer substrates or cover material surfaces with characteristics suited to separation, such as electrophoretic separation. For example, characteristics suited to electrophoretic separation include the properties shown below. Monomeric compounds that confer any of these characteristics can be used in the present invention:

inhibit the substrate adsorption of substances to be separated have affinity for substances to be separated When the substrates or cover materials are made of plastics, forming the above described surface-polymerized membranes or polymer-bound membranes can be difficult, but plasma polymerization allows the formation of plasma-polymerized membranes even on plastic surfaces or finely grooved surfaces. Moreover, the membranes obtained are extremely homogeneous and especially suited when coating plastics.

Lamination of cover materials onto substrates coated with plasma-polymerized membranes sometimes required improved adhesive strength compared to coating with other polymer membranes; however, the methods for producing microchannel chips of the present invention use masks to minimize the areas on which polymer membranes are formed on substrate surfaces and the like, so the plastics used as described above can achieve optimal adhesive efficacy.

Thus, the methods for producing the microchannel chips of the present invention preferably use channels coated with plasma-polymerized membranes and adopt combinations of the plastics listed above, thereby making it possible to easily achieve high-yield production of microchannel chips with very homogeneously coated channels and excellent strength of adhesion between substrates and cover materials.

Glasses used for capillary electrophoresis easily adsorb proteins on to their surfaces. Substrate adsorption of proteins can be controlled using plasma-polymerized membranes. For example, substrate adsorption of proteins can be controlled by altering substrate hydrophobicity or surface charge.

Monomers conferring plasma-polymerized membranes that satisfy the above mentioned conditions include the substances below ("Plasma polymerization", ed. Yoshihito Nagata, written by Mitsuo Kakuta, Kaoru Nakajima, Masataka Miyamura, Shinzo Morita, et al., Tokyo Kagaku Dozin, 1986):

Alkanes or cycloalkanes include the following compounds:

methane, ethane, propane, butane, isobutane, pentane, isopentane, neopentane, hexane, isohexane, 3-methylpentane, 2,2-dimethylbutane, 2,3-dimethylbutane, heptane, 2,2,3-trimethylbutane, octane, nonane, decane, methane-d1, methane-d2, methane-d3, methane-d4, cyclopropane, cyclobutane, cyclopentane, cyclohexane, methylcyclohexane, cyclooctane, cis-decalin, and trans-decalin.

Alkenes, alkynes, or cycloalkynes include the following compounds:

ethylene, propylene, 1-butene, (Z)-2-butene, (E)-2-butene, 2-methylpropene, 1-pentene, 2-methyl-1-butene, 3-methyl-1-butene, 2-methyl-2-butene, 1-hexene, (E)-2-hexene, (E)-3-hexene, 3-methyl-1-pentene, 2,3-dimethyl-2-butene, 1-heptene, 1-octene, (E)-2-octene, 1-decene, 1,3-butadiene, (Z)-1,3-pentadiene, (E)-1,3-pentadiene, isoprene, 2,3-dimethyl-1,3-butadiene, hexadiene, acetylene, propyne, 1-butyne, 2-butyne, 1-pentyne, 3-methyl-1-butyne, vinylacetylene, cyclopropene, cyclobutene, cyclopentene, cyclohexene, cycloheptene, cyclopentadiene, 1,3-cycloheptadiene, and cyclooctatetraene.

Alcohols, aldehydes, ketones, carboxylic acids, or esters include the following compounds:

methanol, ethanol, 1-propanol, 2-propanol, 1-butanol, 2-butanol, 2-methyl-1-propanol, 2-methyl-2-propanol, allyl alcohol, 1,3-butanediol, 2,3-butanediol, 2,3-epoxy-1-propanol, formaldehyde, acetaldehyde, propionaldehyde, butylaldehyde, valeraldehyde, isovaleraldehyde, acrylaldehyde, crotonaldehyde, glyoxal, acetone, 2-butanone, 2-pentanone, 3-methyl-2-butanone, 3-pentanone, 2-hexanone, 4-methyl-2-pentanone, 2-heptanone, cyclobutanone, cyclopentanone, cyclohexanone, cycloheptanone, cyclooctanone, 4-methyl-3-penten-2-one, 2,3-butadione, formic acid, acetic acid, propionic acid, butyric acid, isobutyric acid, acrylic acid, methyl formate, ethyl formate, propyl formate, butyl formate, isobutyl formate, methyl acetate, ethyl acetate, propyl acetate, isopropyl acetate, butyl acetate, isobutyl acetate, s-butyl acetate, methyl propionate, methyl butyrate, vinyl acetate, and allyl acetate.

Ethers, amines and other compounds that can be used as monomer substances include the following:

dimethyl ether, diethyl ether, dipropyl ether, diisopropyl ether, dibutyl ether, ethylene oxide, 1,3-dioxolane, 1,3-dioxane, 1,4-dioxane, methyl vinyl ether, methylamine, ethylamine, propylamine, isopropylamine, butylamine, isobutylamine, s-butylamine, t-butylamine, pentylamine, hexylamine, dimethylamine, trimethylamine, diethylamine, triethylamine, dipropylamine, diisopropylamine, tripropylamine, dibutylamine, allylamine, formamide, acetamide, N-methylacetamide, N,N-dimethylformamide, N,N-dimethylacetamide, methanethiol, ethanethiol, dimethyl sulfide, diethyl sulfide, dipropyl sulfide, dimethyl disulfide, diethyl disulfide, methanedithiol, 1,2-ethanedithiol, nitromethane, nitroethane, 1-nitropropane, 2-nitropropane, 1-nitrobutane, 2-nitrobutane, acetonitrile, propionitrile, acrylonitrile, aminoacetaldehyde dimethylacetal, and hexamethyldisiloxane.

Also, the following halides can be used as monomer substances:

fluoromethane, difluoromethane, fluoroform, tetrafluoromethane (carbon tetrafluoride), vinyl fluoride, 1,1-difluoroethylene, (Z)-1,2-difluoroethylene, (E)-1,2-difluoroethylene, trifluoroethylene, tetrafluoroethylene, 1,1,4,4-tetrafluorobutadiene, perfluorobutadiene, 2-fluoroethanol, trifluoroacetic acid, 1,1,1-trifluoro-2-propanone, perfluoroacetone, chloromethane, dichloromethane, chloroform, tetrachloromethane (carbon tetrachloride), chloroethane, 1,1-dichloroethane, 1,2-dichloroethane, 1-chloropropane, 2-chloropropane, 1,2-dichloropropane, 1,3-dichloropropane, 1-chlorobutane, 2-chlorobutane, 1-chloro-2-methylpropane, 2-chloro-2-methylpropane, chlorocyclopropane, 1,1-dichlorocyclopropane, vinyl chloride, 1,1-dichloroethylene, (Z)-1,2-dichloroethylene, (E)-1,2-dichloroethylene, trichloroethylene, tetrachloroethylene, 3-chloropropene, 1,3-dichloropropene, chloroacetylene, dichloroacetylene, 1-chloropropyne, 2-chloroethanol, chloroacetaldehyde, chloroacetonitrile, dichloroacetonitrile, trichloroacetonitrile, bromomethane, dibromomethane, bromoform, tetrabromomethane (carbon tetrabromide), bromoethane, 1,1-dibromoethane, 1,2-dibromoethane, 1-bromopropane, 2-bromopropane, 1,3-dibromopropane, 1-bromobutane, 2-bromobutane, 1-bromo-2-methylpropane, 2-bromo-2-methylpropane, 1,4-dibromobutane, 1-bromobicyclo[2.2.1]heptane, 1-bromobicyclo[2.2.2]octane, vinyl bromide, 3-bromopropene, 1,3-dibromopropene, bromoacetylene, dibromoacetylene, 1-bromopropyne, 2-bromoethanol, iodomethane, diiodomethane, iodoform, tetraiodomethane (carbon tetraiodide), iodoethane, 1-iodopropane, 2-iodopropane, 1-iodobutane, 2-iodobutane, 1-iodo-2-methylpropane, 2-iodo-2-methylpropane, 1-iodopentane, 3-iodopropene, iodoacetylene, diiodoacetylene, 2-iodoethanol, 1-bromo-2-chloroethane, 1,1,1-trifluoro-2-iodoethane, 2-chloro-1,1-difluoroethylene, 1-chloro-1,2,2-trifluoroethylene, 1,1-dichloro-2,2-difluoroethylene, 1-bromo-2-chloroacetylene, 1-chloro-2-iodoacetylene, and 1-bromo-2-iodoacetylene.

Further, the following aromatic hydrocarbons can be used as monomer substances:

benzene, toluene, ethylbenzene, propylbenzene, cumene, butylbenzene, s-butylbenzene, t-butylbenzene, o-xylene, m-xylene, p-xylene, o-diethylbenzene, m-diethylbenzene, p-diethylbenzene, mesitylene, 1,2,4,5-tetramethylbenzene, styrene, phenylacetylene, (E)-1-propenylbenzene, (E)-1-phenylbutadiene, 2-phenylbutadiene, biphenyl, naphthalene, 1-methylnaphthalene, 2-methylnaphthalene, anthracene, phenanthrene, pyrene, naphthacene, chrysene, and pentacene.

In addition, the following benzene derivatives are useful as monomeric substances of the present invention:

phenol, benzaldehyde, acetophenone, anisole, benzylmethylether, aniline, benzylamine, thiophenol, benzonitrile, fluorobenzene, chlorobenzene, bromobenzene, iodobenzene, o-dichlorobenzene, m-dichlorobenzene, p-dichlorobenzene, o-dibromobenzene, m-dibromobenzene, p-dibromobenzene, trifluorobenzene, hexafluorobenzene, o-fluorotoluene, m-fluorotoluene, p-fluorotoluene, o-chlorotoluene, p-chlorotoluene, o-bromotoluene, p-bromotoluene, o-iodotoluene, m-iodotoluene, p-iodotoluene, p-chlorofluorobenzene, and o-chloroiodobenzene.

Also, the following heterocyclic compounds can be used as monomer substances:

pyridine, 2-methylpyridine, 3-methylpyridine, 4-methylpyridine, 2,6-dimethylpyridine, 2,5-dimethylpyridine, 2,4-dimethylpyridine, pyridazine, pyrimidine, pyrazine, 1,3,5-triazine, pyridine N-oxide, 2-methylpyridine N-oxide, 3-methylpyridine N-oxide, 4-methylpyridine N-oxide, 2,6- dimethylpyridine N-oxide, furan, methylfuran, tetrahydrofuran, pyrrole, pyrrolidine, thiophene, and 2-chlorothiophene.

In addition, troponoid compounds such as tropone and tropolone, and organic metal compounds such as tetramethylsilane, tetramethyltin, and tetramethyl lead, can also be used as monomeric substances.

Of those listed above, acetonitrile and hexadiene can be preferably used when the net charge of the substrate surface is nearly zero at around neutral pH.

Hexamethyldisiloxane can be preferably used when the net charge of the substrate surface is negative around neutral pH.

Hexylamine and aminoacetaldehyde dimethylacetal can be preferably used when the net charge of the substrate surface is positive around neutral pH.

Conditions for forming the plasma-polymerized membranes using these monomer substances are known. Specifically, conditions such as flow velocity, electric discharge power, electric discharge time, and pressure are considered important as primary factors affecting the repeatability of plasma polymerization reactions. In plasma polymerization, optimal polymerization conditions must be tailored to the apparatus and monomer. There is a report that if the W/FM values (where W is the electric discharge power, F is the flow velocity, and M is the molecular weight of the monomer) are the same, the qualities of the membranes are similar (Yasuda, Plasma Polymerization, Academic Press, New York, 1985).

Considering the monomeric substances used and the thickness of the plasma-polymerized membrane ultimately required, those skilled in the art routinely adjust these conditions appropriately. Also, some literature shows the effects of various parameters on the characteristics of plasma-polymerized membranes (Surface and Coatings Technology 82:1-15, 1996, Polymer Engineering and Science 37/7:1188-1194, 1997). In order to fabricate plasma-polymerized membranes with hexamethyldisiloxane, which is an advantageous monomeric substance when aiming to immobilize polynucleotides as described below, optimal conditions within the following range may be selected to give plasma-polymerized membranes of approximately 0-240 Å:
Flow rate: 0 to 50 $cm^3$/min
Discharge power: 0 to 300 W
Pressure: $10^{-6}$ to 10 Torr
Discharge time: 0 to 5 minutes
(Temperature: 0° C. to 100° C.)

Alternatively, the following conditions are more preferable for the formation of plasma-polymerized membranes of approximately 0-240 Å:
Flow rate: 0 to 50 $cm^3$/min
Discharge power: 20 to 100 W
Pressure: 0.05 to 0.6 Torr
Discharge time: 30 seconds to 5 minutes
(Temperature: room temperature)

Such plasma polymerization procedures confer various functional groups on substrate surfaces through selection of monomeric substances, and thus enable the convenient formation of membranes with various properties. For example, various substrates with different surface charge densities or hydrophobicities/hydrophilicities can be obtained.

For example, zeta potentials, which represent the charged state of a material vary with pH and can be preferably controlled within the range of −100 mV to +100 mV.

In addition, for example, the contact angle of a surface can be controlled preferably within the range of 1° to 140°.

The membrane thickness of such plasma-polymerized membranes preferably ranges from 1 nm to 200 nm, for example.

Plasma-polymerized membranes obtained this way are highly homogeneous, and pinhole formation is notably suppressed.

Plasma polymerization also enables the formation of plasma-polymerized membranes on substrate surfaces of arbitrary shape.

The functional groups introduced can be used to variously interact with proteins, enabling a variety of separation methods. For example, when the monomeric compound is an organic substance with nitrogen atoms such as acetonitrile, it is known that plasma-polymerized membranes with amino groups on their surface can be synthesized. Such plasma-polymerized membrane-coated surfaces enable electrostatic interactions (between positively charged membranes and negatively charged proteins), and can be used for protein electrophoresis.

Alternatively, plasma-polymerized membranes with carboxyl groups on their surfaces can be synthesized when a carboxylic acid such as acetic acid or an organic substance such as an ester is used as the monomeric substance. This enables electrophoretic separations or such based on interactions between a negatively charged membrane and positively charged proteins.

Alternatively, plasma-polymerized membranes with highly hydrophobic surfaces enable separations based on hydrophobic interactions and are synthesized when alkane, cycloalkane, or aromatic hydrocarbons are used as monomeric substances. Specifically, the three types of polymerization methods described above enable the creation of surfaces with effects comparable to those of anion exchange chromatography, cation exchange chromatography, and hydrophobic chromatography, respectively.

The methods for producing microchannel chips according to the present invention comprise the steps of: shielding a substrate surface on which channels have been formed using a mask that exposes the entirety of the channels; and forming a polymer membrane on the exposed surface of the substrate; however, the microchannel chips can be mass-produced by simultaneous transfer of photomask patterns using light (Photofabrication: Kiyoshi Naraoka, Kooji Nihei, "Photoetching and Microprocessing", Sogo Electronics Press, 1989).

Using photofabrication, devices such as very large scale integration (VLSI) chips, which are assembled from millions of parts, can be constructed as one piece on silicon substrates of a few millimeters per side. Furthermore, combinations of multiple photomask patterns can be used in photofabrication. Use of this feature enables integration of multiple different treatment processes, such as adhesive application processes and surface treatments.

The photofabrication technologies used for surface modification and thin membrane formation are dry processes. The plasma polymerization methods described above are dry processes, and can thus be used suitably to produce devices by photofabrication. Furthermore, with plasma polymerization, thin membranes having functional groups on their surfaces can be obtained by selecting proper monomeric substances. In addition, plasma-polymerized membranes have highly cross-linked pinhole-free structures, and can thus be used suitably as thin membranes to modify the inside of channels.

Surface-Polymerized Membranes

Surface-polymerized membranes are obtained by polymerizing monomers on substrate surfaces, described above.

Polymerization is preferably performed by polymerizing polymerizable monomers with hydrophobic functional groups having a terminal double bond on the substrate surface.

The hydrophobic functional groups described above include alkenyl groups with terminal double bonds, comprising preferably two to six carbon atoms, more preferably three to six carbon atoms, particularly preferably four to six carbon atoms.

Such hydrophobic functional groups include vinyl groups, allyl groups, 1-butenyl groups, 1-pentenyl groups, and 1-hexenyl groups.

When polymerizable monomers are polymerized with such hydrophobic functional groups, the surface-polymerized membranes are covalently linked by single carbon-carbon bonds, with the hydrophobic functional groups as spacers.

Therefore, in the substrates bound with such surface-polymerized membranes, the hydrophobic spacers prevent water molecules becoming close, and this prevents the release of the hydrophobic spacers themselves due to hydrolysis caused by effects such as pH. In addition, the hydrophobic spacers and the surface-polymerized membranes are linked by carbon-carbon bonds, and thus the surface-polymerized membranes do not detach from the hydrophobic spacer at binding sites.

Thus, when substances to be analyzed are proteins, the surface-polymerized membranes do not detach due to the effect of pH, even when analyzed in aqueous solvents, and thus analyses can be highly reliable.

In surface polymerization methods binding to substrate surfaces can be efficient since surface polymer membranes are formed by polymerizing polymerizable monomers, and thus polymer aggregation is negligible compared to when binding the polymers themselves.

The hydrophobic functional groups can be introduced onto substrate surfaces by dissolving compounds which provide the above-described hydrophobic functional groups having a terminal double bond, using solvents such as toluene, methanol or ethanol, and then contacting the compounds with substrates such as glass. The contact reaction can be carried out, for example, at temperatures ranging from room temperature (about 25° C.) to about 100° C., for approximately one to 24 hours.

The above-described compounds, from which hydrophobic functional groups having a terminal double bond are derived, preferably have at one end a group that is reactive to silanol groups on glass surfaces. Such compounds include, for example, alkenylsilanes such as triethoxyvinylsilane, triethoxyallylsilane, triethoxybutenylsilane, triethoxypentenylsilane, and triethoxyhexylsilane.

Of the compounds listed above, triethoxyallylsilane, triethoxybutenylsilane, triethoxypentenylsilane, and triethoxyhexylsilane are more preferred, and triethoxybutenylsilane, triethoxypentenylsilane, and triethoxyhexylsilane are particularly preferred. These alkenyl silanes are commercially available or can be produced by conventional methods. For example, such compounds can be readily synthesized by reacting a Grignard's reagent or alkyl lithium compound containing the desired alkenyl group with halogenated silane such as chlorosilane or alkoxysilane in a solvent.

The type of polymerizable monomer described above is not limited, as long as it has a vinyl group, an allyl group, a diene, or the like.

Such polymerizable monomers include nonionic monomers, anionic monomers, and cationic monomers.

Nonionic monomers used to produce nonionic (hydrophobic, hydrophilic, etc.) surfaces include, for example:
amides, such as acrylamide and methacryl amide;
esters, such as methyl acrylate, methyl methacrylate, vinyl acetate, allyl acetate, allyl acetoacetate, trimethyl vinyl acetate, vinyl formate, vinyl hexanoate, vinyl laurate, vinyl methacrylate, vinyl octanoate, vinyl palmitate, vinyl pivalate, vinyl propionate, vinyl stearate, mono-2-(methacryloyloxy) ethyl hexahydrophthalate, mono-2-(methacryloyloxy)ethyl phthalate, vinyl benzoate, p-vinyl benzoate, vinyl butyrate, vinyl caprate, vinyl caproate, vinyl crotonate, vinyl decanoate, vinyl cinnamate, allyl butyrate, allyl benzoate, allyl n-butyrate, allyl n-caprate, allyl n-caproate, allyl enanthate, allyl heptanoate, allyl isophthalate, allyl isothiocyanate, allyl isovalerate, and allyl n-valerate;
ketones, such as vinyl methyl ketone;
ethers, such as vinyl butyl ether, allyl ether, allyl ethyl ether, allyl butyl ether, vinyl ethyl ether, and allyl n-decanoate;
alcohols, such as vinyl alcohol and allyl alcohol;
halides, such as vinyl chloride, allyl chloride, methacryloyl chloride, vinyl chloroacetate, acryloyl chloride, allyl bromide, allyl iodide, allyl chloroacetate, allyl chloroformate, and allyl chloroformate;
aromatic compounds having a benzene ring, such as styrene, allyl benzene, 4-methacryloxy-2-hydroxybenzophenone, vinyl toluene, allyl benzyl ether, 4-allyl-2,6-dimethoxyphenol, allyl alisol, and 4-allyl-1,2-dimethoxybenzene;
silanes, such as 3-methacryloxypropyl trimethoxysilane, vinyl trichlorosilane, allyl chlorodimethyl silane, and allyl chloromethyl dimethyl silane;
cyanides, such as methacrylonitrile, vinyl acetonitrile, acrylonitrile, allyl cyanoacetate, and allyl cyanide;
cycloalkane derivatives, such as 2-allyl cyclohexanone, 1-allyl cyclohexanol, and allyl cyclopentane; and
vinyl anthracene, vinyl sulfone, allyl alcohol propoxylate, allyl-L-cysteine, allyl ethylene, allyl glycidyl ether, allyl trifluoroacetate, allyl cyclopentadienyl nickel, allyl diethyl phosphonoacetate, allyl diphenylphosphine, allyl diphenylphosphine oxide, and allyl disulfide.

Of the compounds listed above, acrylamide and vinyl alcohol can be preferably used for hydrophilic nonionic surfaces, and styrene and allyl benzene can be preferably used for hydrophobic nonionic surfaces.

Anionic monomers used to produce anionic surfaces include, for example, carboxyl group-containing compounds such as acrylic acid, methacrylic acid, mono-2-(acryloyloxy) ethyl succinate, and
sulfonate group-containing compounds such as allyl sulfonate, vinyl sulfonate, 2-acrylamide-2-methyl propane sulfonate, 3-allyloxy-2-hydroxy-1-propane sulfonate, and p-vinyl benzene sulfonate.

Of the compounds listed above, vinyl sulfonate and allyl sulfonate can be preferably used as strong anionic compounds; and acrylic acid and methacrylic acid can be preferably used as weak anionic compounds.

Cationic monomers used to produce cationic surface include, for example:
primary amines such as allylamine, 3-acrylamide-N,N-dimethylpropyl amine, allyl cyclohexylamine, and 3-methacrylamide-N-dimethylpropyl amine;
secondary amines such as methyl allylamine;
tertiary amines such as N-allyl diethylamine and N-allyl dimethylamine;
quaternary ammonium salts such as allyl triethyl ammonium, (3-acrylamide propyl) trimethyl ammonium chloride, vinyl trimethyl ammonium bromide, 3-(methacryloylamino) propyl trimethyl ammonium chloride, methacrylic acid ethyl trimethyl ammonium chloride, and diallyl dimethyl ammonium.

In addition to the nonionic monomers, anionic monomers, and cationic monomers listed above, compounds having heterocyclic ring groups in their side chains can also be used, which include, for example, allyl hydrazine, 2-vinyl pyrazine, 2-vinyl pyridine, 4-vinyl pyridine, N-vinyl-2-pyrrolidone, 1-allyl benzotriazole, and allyl-1-benzotriazole carbonate.

Of the compounds listed above, diallyl dimethyl ammonium salts or such can be preferably used as strong cationic compounds, and allylamine or such can be preferably used as a weak cationic compound.

Such polymerizable monomers may be used individually or in combination.

The polymerizable monomers listed above can be polymerized on substrate surfaces by radical polymerization using conventional methods. For example, polymerization initiators may be added as necessary, in the presence or absence of solvents, and polymerizable monomers can be polymerized on substrate surfaces onto which polymerizable functional groups have been introduced.

The solvents are not limited as long as they dissolve a polymerizable monomer. For example, THF, methanol, DMF, or DMSO can be used.

Polymerization initiators include, for example, 2,2'-azobis (isobutyronitrile) (AIBN), 1,1'-azobis(cyclohexane-1-carbonitrile), and 2,2'-azobis(2-methylbutyronitrile). In addition to these azo compounds, peroxide and organic metal compounds can also be used.

Polymerizable monomers that do not dissolve in solvents such as THF described above can be polymerized using, for example, ultrapure water as the solvent and polymerization initiators such as N,N,N',N'-tetramethyl ethylenediamine or 4,4'-azobis cyanovalerate.

The polymerization conditions are not limited and depend on the types of polymerizable monomers used. Typically, polymerization is carried out at, for example, temperatures ranging from room temperature to around 100° C., for approximately one to 72 hours.

The surface-polymerized membranes obtained by this method can have hydrophobic/hydrophilic surfaces and various electric charges, depending on the type of polymerizable monomers, or combinations of polymers used.

For example, zeta potentials, which represent the charged state of a material, vary with pH and can be suitably controlled within the range of −100 to +100 mV.

In addition, for example, surface contact angles can be suitably controlled within the range of 1° to 140°.

Surface-polymerized membranes sometimes contain unmodified portions such as pinholes. Thus, polymerizable monomers or polymers may be further attached.

Additional polymers or monomers may be reacted with the functional groups in the polymer side chains of the surface-polymerized membranes that can be used in the present invention.

Proteins can be separated by electrophoresis using various interactions between proteins and the introduced functional groups. For example, surface-polymerized membranes with cationic functional groups on their surface can be synthesized by using any one of the cationic monomers described above as the polymerizable monomer. By using surfaces coated with such surface-polymerized membranes, protein electrophoresis can be carried out using electrostatic interactions (between negatively charged proteins and positively charged membranes).

Alternatively, surface-polymerized membranes with anionic functional groups on their surface can be synthesized using anionic monomers as the polymerizable monomers. Such membranes enable electrophoretic separation based on interactions between negatively charged membranes and positively charged proteins.

Further, since highly hydrophobic or hydrophilic surface-polymerized membranes can be synthesized using properly selected nonionic polymerizable monomers, separation based on hydrophobic or hydrophilic interactions is possible.

Specifically, the three types of membranes exemplified above enable the creation of surfaces with effects comparable to those of anion exchange chromatography, cation exchange chromatography, and hydrophobic/hydrophilic chromatography, respectively.

Polymer-Bound Membranes

Polymer-bound membranes can be produced by introducing reactive functional groups onto substrate surfaces and covalently linking polymers to the functional reactive groups.

Reactive functional groups that link with polymer compounds include amino groups, epoxy groups, carboxyl groups, and aldehyde groups. Of these groups, amino groups and epoxy groups can be preferably used.

Linkage groups comprising such reactive functional groups are preferably linked to substrate surfaces via hydrophobic spacers.

Hydrophobic spacers contain alkyl groups comprising preferably two to six carbon atoms, more preferably three to six carbon atoms, and particularly preferably four to six carbon atoms.

Such substrates with polymer compounds, to which reactive functional, groups are bound via hydrophobic spacers, prevent the peeling of polymer-bound membranes caused by hydrolysis due to effects such as pH because the hydrophobic spacers prevent water molecules from becoming close to the substrate.

Depending on the type of substrate, the above-described reactive functional groups with spacers can be introduced onto substrate surfaces using, for example, a silane-coupling method when the substrate is a glass, and a self-assembled monolayer method when the substrate is a metal.

When a silane-coupling method is used, the functional groups can be introduced by, for example, contacting a substrate such as glass with an amino alkyl-type silane-coupling reagent such as aminopropyl triethoxysilane, aminobutyl triethoxysilane, aminopentyl triethoxysilane, aminohexyl triethoxysilane, or an epoxy alkyl-type silane-coupling reagent such as 3-glycidoxypropyl triethoxysilane, 3-glycidoxybutyl triethoxysilane, 3-glycidoxypentyl triethoxysilane, or 3-glycidoxyhexyl triethoxysilane, that has been dissolved in a solvent such as toluene, methanol, or water. These reagents are commercially available or can be produced by conventional methods. For example, the amino alkyl-type silane-coupling reagents or epoxy alkyl-type silane-coupling reagents can be readily synthesized by reacting a Grignard's reagent or an alkyl lithium compound containing the desired alkyl group and functional group with a halogenated silane such as chlorosilane or alkoxysilane in the presence of a solvent.

The contact reactions can be carried out, for example, at temperatures ranging from room temperature (about 25° C.) to about 100° C., for approximately one to 24 hours.

When a self-assembled monolayer method is used, polymer-bound membranes can be formed by, for example, coating substrate surfaces with thin metallic membranes of gold or the like by sputtering or such, introducing spacers having functional groups and thiol groups onto the surface of the thin metallic membrane, and then reacting polymers with the surface. Alternatively, polymerization initiators may be reacted with the functional groups to polymerize monomers. Also, polymer membranes may also be formed by modifying the metallic surface with pre-prepared polymers comprising thiol groups.

The metals include gold, silver, and copper. The spacers include aminoethanethiols comprising amino groups and thioctic acids comprising carboxyl groups.

Solvents for introducing spacers or polymers comprising thiol groups to substrates can dissolve the spacers in solvents such as DMSO or water, and then contact the spacers with the thin metallic membrane.

The contact reaction is carried out at, for example, temperatures ranging from room temperature to about 100° C., for approximately one to 24 hours.

Examples of the above-described polymers include polymers prepared in advance from polymerizable monomers using the surface polymerizations described above. Of these polymers, polystyrene, polyallylbenzene, polyvinyl alcohol, polyacrylamide, polyvinyl sulfonate, polyacrylic acid, polydiallyl dimethylammonium salt, polyallylamine, polyethylene glycol, or such can be used preferably.

Of the polymers listed above, polyvinyl alcohol and polyallyl alcohol can be preferably used for nonionic surfaces.

Polyacrylic acid can be used more preferably for powerful anionic surfaces.

Polyallylamine can be used more preferably for powerful cationic surfaces.

Such polymers may be used individually or in combination.

The average molecular weight of such polymers preferably ranges from, for example, 5000 to 500000, and more preferably 10000 to 250000.

Polymer-bound membranes produced by binding polymers to substrates or cover materials sometimes contain polymer-unmodified portions such as pinholes, where the reactive functional groups are not linked to the polymers. Thus, polymers may be further attached.

The methods for producing such polymer-bound membranes are not limited and any known method can be employed for this purpose. For example, such membranes can be produced by dissolving an above-described polymer in a solvent and contacting the polymer solution with a substrate having an above-described surface onto which reactive functional groups have been introduced.

The solvents are not limited, as long as they dissolve polymers. Such solvents include, for example, DMSO (dimethyl sulfoxide) and HEPES (2-[4-(2-hydroxyethyl) 1-piperazinyl] ethane sulfonate) buffer.

In the binding reactions, activators can be used as necessary. For example, to link polyacrylic acid to substrates where amino groups have been introduced, polyacrylic acid is dissolved in HEPES, then N-hydroxy succinimide and 1-ethyl-3-(3-dimethylaminopropyl) carbodiimide hydrochloride are added.

The polymer-bound membranes prepared by the methods described above sometimes have polymer-unmodified portions; however, different polymers may be attached to these polymer-unmodified portions. In addition, different polymers or monomers may be reacted with the functional groups in the side chains of the bound polymers.

In this way polymer-bound membranes with surfaces that have various electrical charges and that are hydrophobic/hydrophilic can be obtained depending on the types of polymers or combinations of multiple polymers.

For example, zeta potentials, which represent the charged state of a material, vary with pH and can be controlled preferably within the range of −100 to +100 mV.

In addition, for example, surface contact angles can be controlled preferably within the range of 1° to 140°.

In such polymer-bound membranes, membrane thickness can be readily controlled by pre-adjusting the polymers to be bound.

Proteins can be separated by electrophoresis or such using various interactions between proteins and introduced functional groups. For example polymer-bound membranes having cationic functional groups on their surfaces can be synthesized by using polymers derived from the above-described cationic monomers. Protein electrophoresis can be carried out using electrostatic interactions (between negatively charged proteins and positively charged membranes) by using surfaces coated with such polymer-bound membranes.

Polymer-bound membranes having anionic functional groups on their surfaces can be synthesized using polymers derived from anionic monomers. Such membranes enable electrophoretic separations or such by using amino group-equivalent electrostatic interactions between positively charged proteins and negatively charged membranes.

Polymer-bound membranes with highly hydrophobic or hydrophilic surfaces can be synthesized using properly selected polymers derived from nonionic polymerizable monomers, and thus separation based on hydrophobic or hydrophilic interactions is enabled.

Alternatively, substrate surfaces having both anionic and hydrophobic (or hydrophilic) properties can be formed by modifying polymers containing anionic functional groups, and then linking nonionic polymers or nonionic monomers having, for example, hydrophobic (or hydrophilic) functional groups, to the anionic functional groups. Furthermore, the balance of hydrophobicity (or hydrophilicity) can be controlled by adjusting the degree of modification with nonionic polymers or monomers.

The microchannel chips thus obtained show excellent adhesive strength when laminating substrates with cover materials since there are some areas of substrate surface, more preferably some areas on the substrate surface and cover material surface, that are not coated with polymer membrane.

Microchannel Chips

The microchannel chips of the present invention are made by laminating cover materials onto the channel-side surfaces of substrates on which the channels are formed, wherein a part or an entire surface of the channels on the substrate surface is coated with a polymer membrane.

Further, the substrate side surfaces of the above cover materials are preferably coated with polymer membranes.

Furthermore, it is more preferable that the areas on the substrate-side surfaces of the cover materials, which are opposite the substrate areas on which the polymer membranes are formed, are coated with polymer membranes that are partially or entirely identical in shape to those in the part of the substrate on which polymer membrane is formed.

Such microchannel chips are preferably produced by the methods for producing microchannel chips of the present invention.

The substrates, cover materials, channels, and polymer membranes have the same meanings as those presented in the methods for producing microchips described above.

Methods for Separating Biomolecules

The methods for separating biomolecules of the present invention comprise the following steps of:
a) adding biomolecules to be analyzed to microchannel chips which are made by laminating the channel-side surface of a substrate on which channels have been formed with a cover material, wherein the surfaces of the channels on the substrate surface are coated with a polymer membrane; and
b) applying separation pressure to a separating medium.

Microchannel chips usable in the methods for separating biomolecules are the microchannel chips of the present invention. Further, the substrates, cover materials, channels, and polymer membranes have the same meanings as those presented in the methods for producing microchips described above.

The separation media include but are not limited to known electrophoresis media. The separation media include, for example, organic solvents, gels such as polyacrylamide and agarose, and liquids such as buffers. Preferred separation media are electrophoretic media. Preferred electrophoretic media include, for example, gels and buffers. The type of separation medium to be used in pressure feeds is not limited.

The separation pressure, which varies with the separation medium used and such, is not particularly limited. Electrophoresis, pressure feeds, or the like can be employed. Of these, electrophoresis is preferable.

Biomolecules include proteins, DNAs, viruses, bacteria, sugars, amino acids and other metabolites, and of these, the present invention is effective for separating proteins.

The separation principles of the electrophoretic methods described above are not limited. In electrophoretic separations that use the above-mentioned substrates whose surfaces are coated with polymer membranes, separation is possible based on various properties, depending on the conditions of the separation medium. Separation conditions in electrophoresis include pH gradients, molecular sieving, and interactions with the contacting functional groups in a separation medium. Isoelectric focusing involves electrophoresing proteins in a separation medium with a pH gradient. Molecular sieving electrophoresis under denaturing conditions involves electrophoresing proteins in a medium having a molecular sieving effect, such as a polyacrylamide gel, in the presence of a protein denaturant such as SDS, urea, or guanidine. When no denaturant is used this is called native gel electrophoresis.

Similarly, nucleic acids are fractionated by their length during electrophoresis based on molecular sieving effects. Analytical methods such as PCR-SSCP are also known, in which the same nucleic acids are separated by electrophoresis under both non-denaturing and denaturing conditions, and then a comparison of both results reveals differences in conformation.

Furthermore, separation media containing various functional groups can also be used. Specifically, such media include substances with affinities resulting from electrostatic interaction, hydrogen bonding, or hydrophobic bonding, or any combination of these. Such substances with affinities include combinations such as antigen-antibody, hybrids of nucleic acids comprising complementary nucleotide sequences, avidin-biotin, and sugar-lectin.

One of the electrophoretic principles suitable for the present invention is capillary electrophoresis. When performing capillary electrophoresis of the present invention, the above polymerized membranes enable channels to be formed that can control electroosmotic flow.

In the present invention, monomeric substances suitable for use in capillary electrophoresis in the case of plasma-polymerized membranes include, for example, hexadiene, hexamethyldisiloxane, acetonitrile, hexylamine, and aminoacetaldehyde dimethylacetal.

Monomeric substances suitable for surface-polymerized membranes include styrene, acrylamide, vinyl sulfonate, acrylic acid, diallyl dimethyl ammonium salt, and allylamine.

Monomeric substances suitable for polymer-bound membranes include polyvinyl alcohol; polyacrylic acid, and polyallylamine.

The following is an example of electrophoresis using a plasma-polymerized membrane. After an anolyte and a catholyte are loaded onto the respective ends, voltage is applied across both ends. The anolyte is an acidic solution which gives a pH lower than the pKa of the most acidic electrolyte in the solution. On the other hand, the catholyte is an alkaline solution which gives a pH higher than the pKa of the most basic electrolyte in the solution. Each of the ampholytes moves to the position of their isoelectric points and then stop. Protein components are concentrated at their isoelectric point positions along the pH gradient in the channels, and are observed as narrow zones.

In capillary zone electrophoresis (CZE), when a solution containing a single electrolyte is introduced into a channel, an electric double layer is formed between the inner wall of the channel and the electrolyte solution in contact with the inner wall. Upon application of a voltage, electrolytes move together with the solvent, causing an electroosmotic flow. The electroosmotic flow is a driving force that moves the separated ionic components. Components of a sample are attracted to either electrode by electrostatic forces, according to their net charges and sizes, and are separated as a result of differential mobility due to differences in net charge and size.

In CZE biomolecules are separated using electroosmotic flow; however, CZE is problematic because electrophoretic flow varies widely depending on pH, and individual differences also exist between capillaries. If this electrophoretic flow can be controlled, biomolecules may be Separated by various modes (general capillary electrophoresis (such as CZE, capillary gel electrophoresis (CGE), capillary isoelectric focusing electrophoresis (CIFE)) and chromatographic separations (such as ion-exchange, reverse phase, normal phase, and affinity chromatography)). The channels coated with polymer membranes (especially plasma-polymerized membranes) used in the present invention are very effective because they can control electroosmotic flow.

Electrophoretic Apparatus

Further, the present invention relates to apparatus for electrophoretic analysis, comprising the following components:
a) microchannel chips made by laminating the channel-side surface of a substrate on which channels have been formed with a cover material, wherein the surface of the channels on the substrate surface is coated with a polymer membrane,
b) supports used to retain the microchannel chips, and
c) electrodes used to apply voltages to the microchannel chips retained by the supports.

The microchannel chips usable in the electrophoretic apparatus are the microchannel chips of the present invention. Further, the substrates, cover materials, channels, and polymer membranes have the same meanings as those presented in methods for producing microchips described above. The supports are not specifically limited, and may be any support on which microchannel chips can be stably fixed.

All prior art literature cited in the present specification is herein incorporated by reference.

EXAMPLES

The present invention will be described by the following Examples, but it is not limited by these Examples. The apparatus and the like used in the Examples are as described below.

[Devices for Plasma Polymerization]

The plasma-polymerized membranes described in the Examples were synthesized using the after-glow plasma polymerization method using a RF power generator and outer electrodes. A modified device was assembled by attaching various units to the plasma reactor model BP-1 from SAMCO, INC. so as to achieve automatic control of flow, pressure, and power matching. The components of the device are listed below:

Reaction chamber: Pyrex® 210 mmφ.
Sample stage: a heater-controlling stage (SUS304) installed under the chamber Exhaust system: turbo molecular pump (Pfeiffer) and rotary pump (Edwards)
RF power generator: crystal oscillator, 13.56 MHz, 300 W (SAMCO, INC.)
Matching: auto-matching system (SAMCO, INC.)
Pressure controller: automatic control of pressure from a baratron vacuum gauge (MKS Instruments) by using the valve unit of an automatic pressure controller (APC) (VAT)
Gas feed system: automatic control of sample monomers, argon, and oxygen line by using electromagnetic valves and mass flow controller (MEC) (STEC)
[Electron Microscope]
    Electron probe microanalyzer—JXA-8100 (JOEL Ltd.)
[Electron Probe Microanalyzer]
    Electron probe microanalyzer—JXA-8100 (JOEL Ltd.)

Example 1

Preparation of Chips on which Plasma-Polymerized Membranes are Formed Using Masks A stainless steel mask of 200 μm width was loaded on polymethyl methacrylate substrates (PMMA) (KRALEX 000 (trade name), Nitto-Jushi, Co. Ltd, 3 mm (thickness)×70 mm (length)×70 mm (width)), and these were then placed in a chamber of a plasma-polymerizing apparatus. The chamber vacuum was $3 \times 10^{-5}$ Torr. The chamber was filled with hexamethyl disiloxane (HMDS) and discharge was carried out at 150 W of discharging power (RF power), 0.1 Pa of pressure, 100 sccm of flow rate for 180 seconds to form a plasma-polymerized membrane. The membrane was 100 nm thick.

Figure 1:
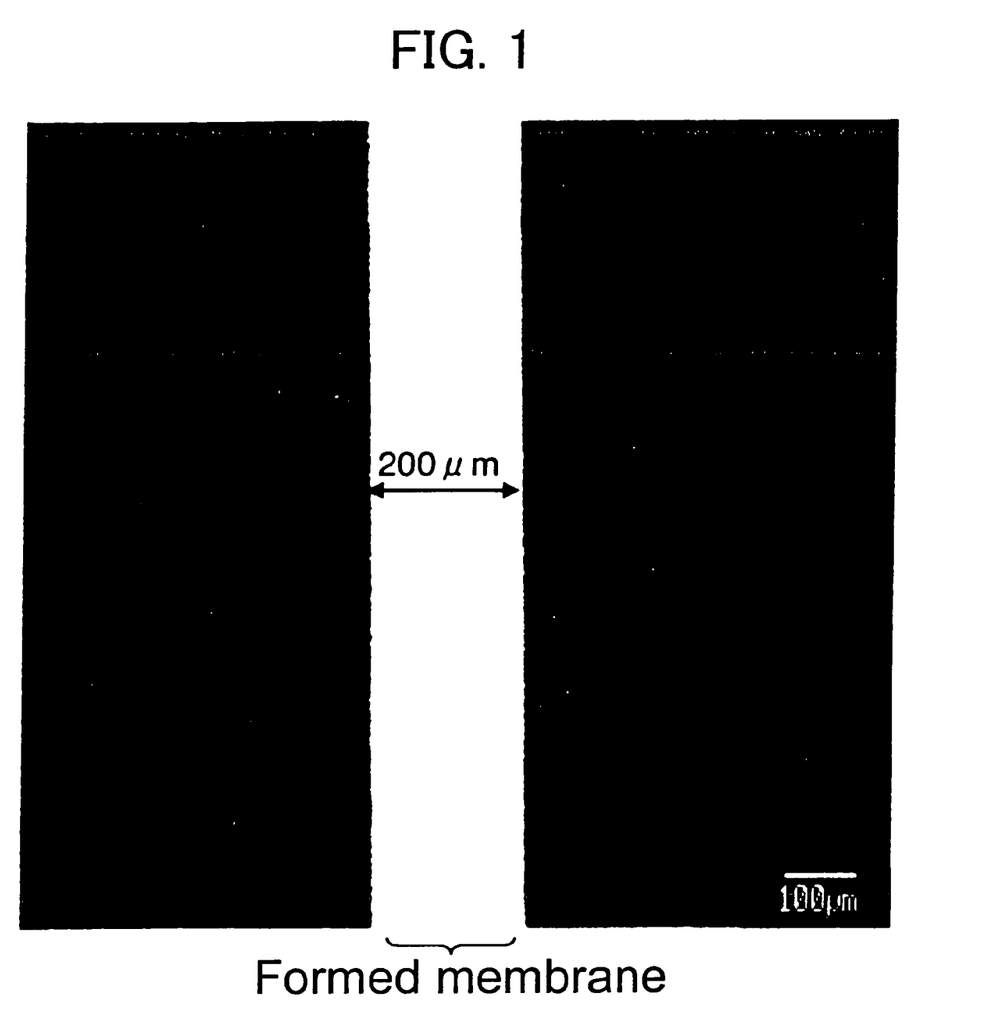
FIG. 1 is an electron microscope photograph showing that a 200 μm wide plasma-polymerized membrane is formed. The accelerating voltage of the electron microscope is 5.00 kV and the photograph is magnified 100 times.

As shown in FIG. 1, observation by electron microscope confirmed the formation of a plasma-polymerized membrane of width 200 μm.

Figure 2:
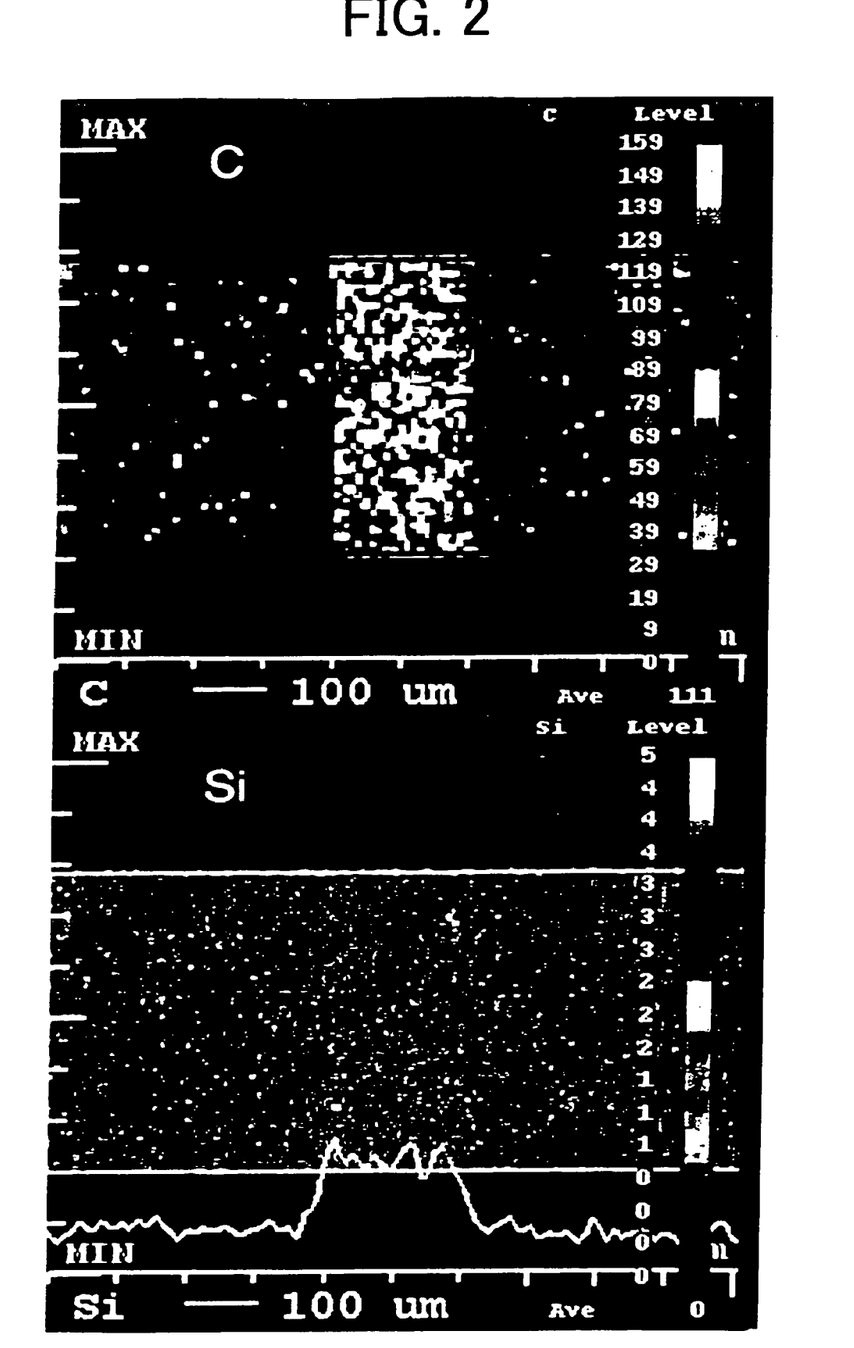
FIG. 2 is a photograph showing an element mapping composition analysis of the formed membrane using an electron probe microanalyzer.

As shown in FIG. 2, element mapping composition-analysis was carried out on the formed membrane using an electron probe microanalyzer, revealing that Si, which was not contained in the PMMA substrate but was contained in HMDS, was strongly detected in the 200 μm width. Further, C, which was hardly contained in HMDS compared to the PMMA substrate, was detected in smaller amounts, thereby confirming that the membrane was formed at mask width.

Example 2

Production of Microchannel Chips

Electrophoretic chips were prepared by laminating formed chips (polymethyl methacrylate; PMMA) with polydimethyl siloxane: PDMS, and these were used to separate proteins.

Figure 3:
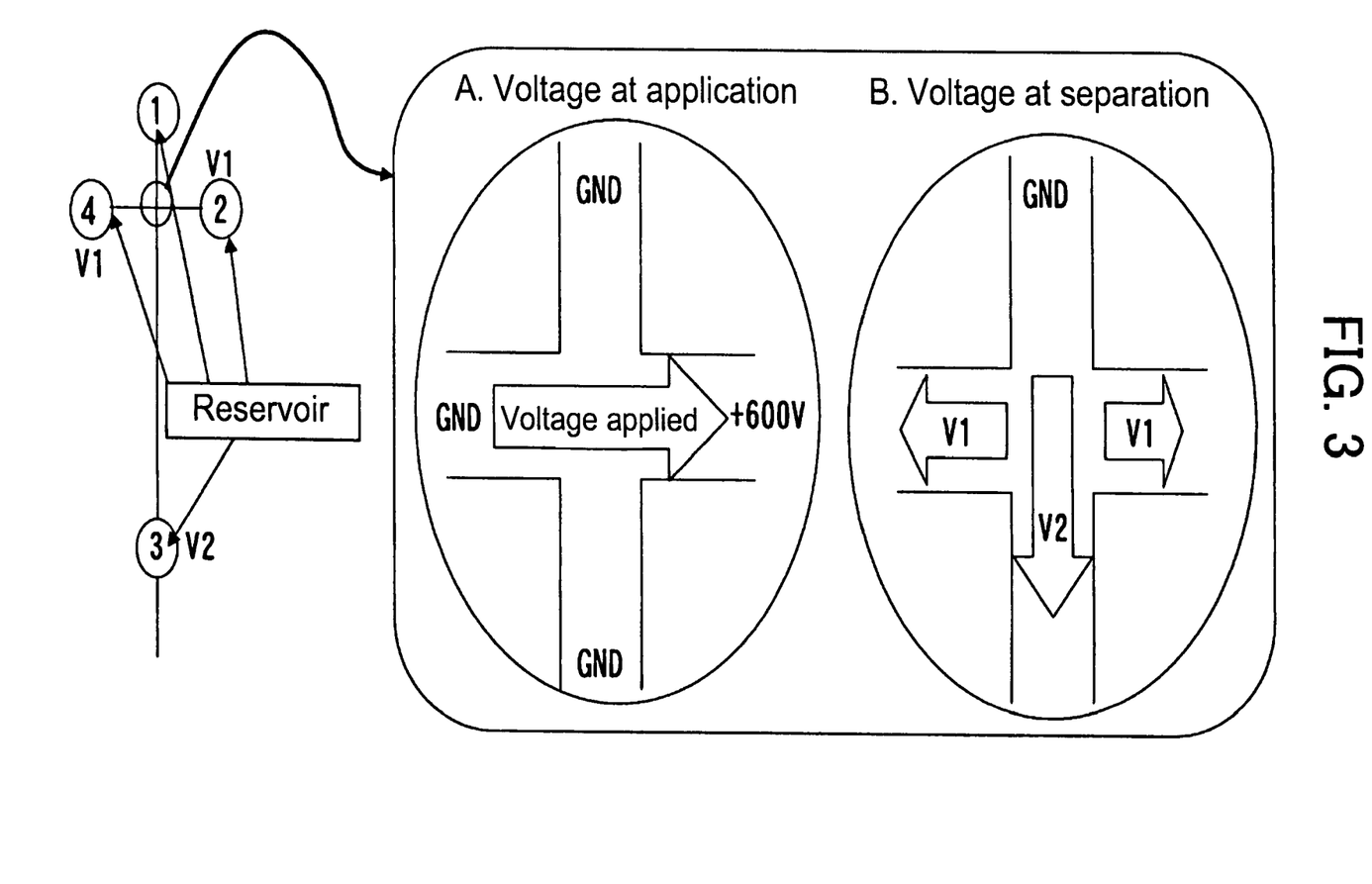
FIG. 3 is a schematic diagram showing how to apply voltage to chips when introducing and separating samples.

Chips (substrates) equipped with cross-shaped microchannels for plasma-polymerization were prepared by injection molding of PMMA (8 mm thickness) (Kobayashi-Seikou, Co., Ltd, see FIG. 3). Depth and width of the microchannels: 100 μm each; diameter of reservoir: 4 mm; inlet channel: 10 mm; and separation channel: 50 mm.

Cover materials were prepared by polymerizing polydimethyl siloxane (PDMS) (trade name: SYLGARD 184: by Shinetsu Silicones) in polystyrene cases. Polymerization was carried out by mixing monomers and catalysts at 10:1, degassing the mixture with a vacuum pump, casting it in a polyethylene case, and reacting it at 70° C. for one hour to yield PDMS, the cover material.

To form membranes within the microchannels of the chips for plasma-polymerization, three types of metal mask were used (widths of 150, 200 and 1000 μm) (made of stainless steel: Kenseido, Co.).

Three types of metal masks (widths of 150, 200 and 1000 μm) were applied to both the substrates and cover materials, and then plasma polymerization was carried out using polymerizable monomers such that the thickness of each plasma-polymerized membrane was approximately 100 nm. HMDS, hexylamine and acetonitrile were used as the polymerizable monomers.

Conditions for plasma-polymerization for each monomer are as described below:
HMDS
    RF power: 150 W
    MF: 100 sccm (value for HMDS, 22.0 sccm for acetonitrile-mass flowmeter)
    Time: 180 seconds
Hexylamine
    RF power: 200 W
    MF: 4.0 sccm (value for acetonitrile-mass flowmeter)
    Time: 900 seconds
Acetonitrile
    RF power: 200 W
    MF: 10.0 sccm (value for acetonitrile-mass flowmeter)
    Time: 180 seconds After forming membranes, the metal masks were peeled off, and then the substrates and cover materials were aligned and laminated to prepare electrophoretic chips.

When phoresis buffer (0.1M phosphate buffer (pH 8.5) containing 0.6% cellulose) was flowed through the microchannels of the prepared microchannel chips, no phoresis buffer leakage to the outside of the channels was found in any of the plasma-polymerized membranes at all widths of 150, 200 and 1000 μm, confirming sufficient lamination of the substrates with the cover materials.

Example 3

Protein Separation by Electrophoresis Using the Microchannel Chips

Separation experiments were carried out using the microchannel chips prepared using the HMDS 1000 μm metal masks in Example 2, and carbonic anhydrase as a protein. Uncoated chips were used as a control.

1 mg of carbonic anhydrase was stained with fluorescence reagent (Cy5) as described below and used.
Methods for Staining Using a Fluorescence Reagent (Methods for Staining Proteins Using Cy5)

Cy5, a fluorescent dye, has been commercialized as kits for protein staining, and is a fluorescence reagent with good stability and quantum efficiency. Therefore, proteins were stained using Cy5 as a fluorescent dye, and then used. Staining procedure was as described below. One mg of carbonic anhydrase (protein weight) (isoelectric point pI=7.3, molecular weight 30 kDa (Sigma K.K.)) and one pack of Amersham Cy5 staining Kit were dissolved in 1 mL of 0.1M carbonate buffer (pH 9.2) and the mixture was reacted at room temperature for one hour while stirring. After the reaction, in order to remove unreacted Cy5, 500 μL of the reaction mixture was placed in Microcon YM3 (Millipore Corporation, fraction molecular weight 3000) and centrifuged at 14,000 G for 100 minutes (ultrafiltration), then 400 μL of the same carbonate buffer was added to the filtrate and this was centrifuged again. This step was repeated four times to purify it. Final fluid volume was adjusted to 1 mL and Cy5-stained proteins were prepared.
Methods for Introducing Phoresis Buffer into Chips As shown in FIG. 3, 17 μL of phoresis buffer was placed in reservoir 3 of the chip and pressure was applied using a syringe to fill the inside of the channel with phoresis buffer (taking care to exclude bubbles).

The insides of the channels extending to each reservoir were filled with phoresis buffer, then 17 µL of phoresis buffer was added to both reservoirs 1 and 2, and 15.5 µl of the same was added to reservoir 4. 1.5 µL of a sample was added to reservoir 4, and stirred well by pipetting.

Electrodes made of platinum wire were placed into each reservoir, and electrophoresis was carried out while controlling voltage using a high voltage sequencer. Electrophoresis was detected in channels immediately before the inlet of reservoir 4. The voltage at application, the voltage at separation, application time and separation time are as described below. The method of voltage application is shown in FIG. 3.

| | | |
|---|---|---|
| Voltage at application | | 600 V |
| Application time | | 60 seconds |
| Voltage at separation | V1 | 130 V |
| | V2 | 750 V |
| Separation time | | 1200 seconds |

Results

Figure 4:
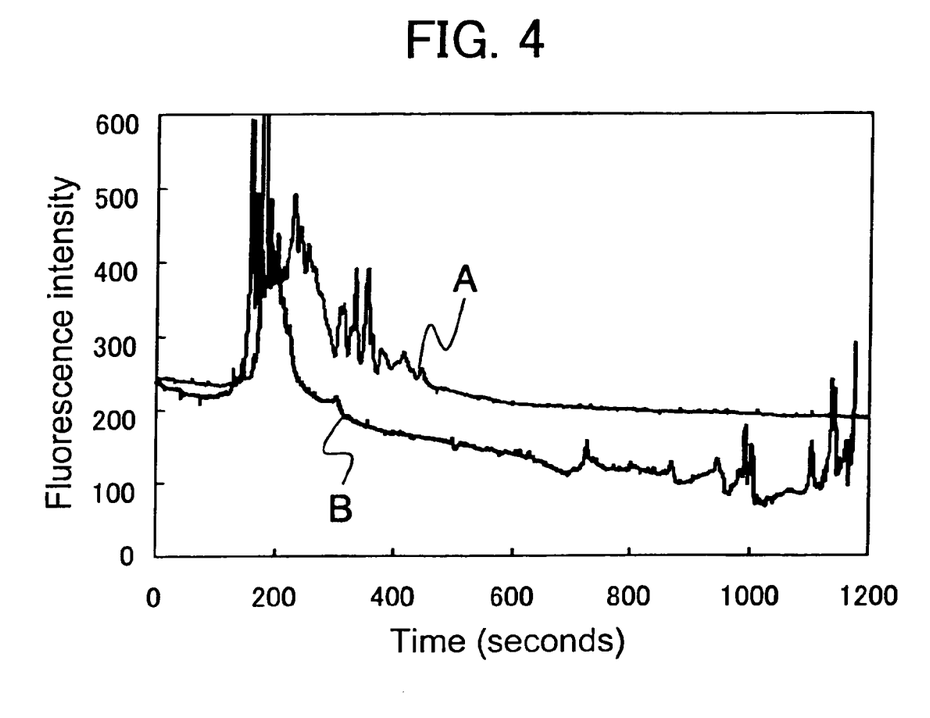
FIG. 4 is a diagram showing the results of electrophoresis of Cy5-stained carbonic anhydrase using chips with plasma-polymerized membranes and with chips without formed membranes.

The results of electrophoresis using carbonic anhydrase as a sample are shown in FIG. 4. The peak detected at the beginning may have resulted from unreacted Cy5 (No membrane formed: about 160 seconds, HMDS formed membranes: about 180 seconds). The multiple peaks subsequently detected may have resulted from carbonic anhydrase. The peak group of chips without formed membranes (about 170 to 1200 seconds) and the other peak group of chips with HMDS formed membranes (about 190 to 460 seconds) were detected at approximately the same time when the Cy5 peak served as a standard (about ten seconds later). More peaks were detected more quickly for chips with HMDS formed membranes, which are thus considered to have better separation efficiency. Separation efficiency as used herein means the differences in electrophoresis patterns and number of peaks (more peaks are construed as higher separation efficiency). Detected protein peaks were examined when the Cy5 peak served as a standard.

INDUSTRIAL APPLICABILITY

In the methods for producing microchannel chips of the present invention, polymer membranes are formed on substrate surfaces, and more preferably on the surfaces of both substrates and cover materials, such that some areas are not coated with polymer membranes, and therefore the methods provide exceptional adhesive strength and convenience when laminating substrates with cover materials.

The invention claimed is:

1. A method for producing a microchannel chip, comprising the steps of:
    a) shielding a surface of a substrate, on which a groove-like channel has been formed, with a mask that exposes the channel,
    b) forming a polymer membrane on the exposed surface of the substrate; and
    c) laminating a cover material on to the substrate surface on which the channel has been formed.

2. The method of claim 1 further comprising the step of forming a polymer membrane on the side of the cover material surface that will be laminated to the substrate.

3. The method for producing the microchannel chip of claim 2, wherein when a polymer membrane is formed on the side of the cover material surface that will be laminated to the substrate, the polymer membrane is formed on an exposed surface of the cover material by shielding the cover material surface with a mask, the exposed area of which is partially or entirely identical in shape to the mask for the substrate.

4. The method of claim 2, wherein the polymer membrane formed on the side of the cover material surface is:
    (a) a plasma-polymerized membrane formed by plasma polymerizing a plasma-polymerizable monomer on the cover material surface,
    (b) a surface-polymerized membrane formed by polymerizing a polymerizable monomer on the cover material surface, or
    (c) a polymer-bound membrane formed by binding a polymer compound onto the cover material surface.

5. The method of claim 2, wherein the polymer membrane formed on the side of the cover material surface is a plasma-polymerized membrane.

6. The method of claim 2, wherein the polymer membrane formed on the exposed substrate surface and the polymer membrane formed on the side of the cover material surface are identical polymer membranes.

7. The method of claim 2, wherein the mask is either a photoresist-mask or a metal mask.

8. The method of claim 1, wherein the polymer membrane formed on the exposed substrate surface is:
    (a) a plasma-polymerized membrane formed by plasma polymerizing a plasma-polymerizable monomer on the substrate surface,
    (b) a surface-polymerized membrane formed by polymerizing a polymerizable monomer on the substrate surface, or
    (c) a polymer-bound membrane formed by binding a polymer compound onto the substrate surface.

9. The method of claim 1, wherein the polymer membrane formed on the exposed substrate surface is a plasma-polymerized membrane.

10. The method of claim 1, wherein the lamination is performed by pressure bonding or thermocompression bonding.

11. The method of claim 1, wherein at least either one of the substrate or the cover material is a plastic.

12. The method of claim 11, wherein one of the substrate or the cover material is a silicon resin, and the other is a glass or a plastic, and the laminating process comprises a method in which the substrate and the cover material are attached by pressure bonding.

13. The method of claim 1, wherein the substrate and the cover material are plastics.

14. The method of claim 13, wherein both the substrate and the cover material are a thermoplastic resin, and the laminating process comprises a method in which the substrate and the cover material are attached by thermocompression bonding.

15. The method of claim 14, wherein thermocompression bonding is performed at 200° C. or less.

16. The method of claim 1, wherein the mask is either a photoresist-mask or a metal mask.

* * * * *